(12) United States Patent
Cote et al.

(10) Patent No.: US 10,702,197 B2
(45) Date of Patent: Jul. 7, 2020

(54) DUAL AMPLITUDE MODULATION AND POLARIZATION FREQUENCY MODULATION AS WELL AS COMPENSATION FOR NONINVASIVE GLUCOSE MONITORING

(71) Applicant: TEXAS A&M UNIVERSITY SYSTEM, College Station, TX (US)

(72) Inventors: Gerard L. Cote, College Station, TX (US); Daniel T. Grunden, Addison, TX (US); Bilal H. Malik, El Cerrito, CA (US); Casey Pirnstill, Bucyrus, OH (US); Erwin Thomas, III, College Station, TX (US)

(73) Assignee: The Texas A&M University System, College Station, TX (US)

( * ) Notice: Subject to any disclaimer, the term of this patent is extended or adjusted under 35 U.S.C. 154(b) by 542 days.

(21) Appl. No.: 15/656,146

(22) Filed: Jul. 21, 2017

(65) Prior Publication Data
US 2018/0028101 A1    Feb. 1, 2018

Related U.S. Application Data

(60) Provisional application No. 62/366,767, filed on Jul. 26, 2016.

(51) Int. Cl.
*A61B 5/1455*   (2006.01)
*A61B 5/145*    (2006.01)
(Continued)

(52) U.S. Cl.
CPC ...... *A61B 5/14558* (2013.01); *A61B 5/14532* (2013.01); *A61B 5/6821* (2013.01);
(Continued)

(58) Field of Classification Search
CPC .............. A61B 5/14558; A61B 5/1455; A61B 5/14555; A61B 5/14532; A61B 5/6821;
(Continued)

(56) References Cited

U.S. PATENT DOCUMENTS

| | | | |
|---|---|---|---|
| 4,035,083 A | * | 7/1977 | Woodriff .................. G01J 3/28 356/368 |
| 5,209,231 A | | 5/1993 | Cote et al. |

(Continued)

OTHER PUBLICATIONS

Yu, et al, "Dual-modulation, dual-wavelength, optical polarimetry system for glucose monitoring," J. Biomed. Opt., Aug. 2016, 8 pages.

*Primary Examiner* — Navin Natnithithadha
(74) *Attorney, Agent, or Firm* — Winstead PC

(57) ABSTRACT

An embodiment relates generally to an improved method and apparatus for modulating the amplitude and rotation of the plane of polarization of linearly polarized light for multiple uses but primarily as part of a noninvasive glucose monitoring system. As compared to previous monitoring systems, an embodiment provides faster monitoring while maintaining or even reducing noise and minimizing system complexity. Embodiments described herein address these concerns with a modulation and compensation approach that both uses a single high speed device and also modulation of the lasers.

20 Claims, 11 Drawing Sheets

(51) Int. Cl.
*A61B 5/00* (2006.01)
*G02F 1/09* (2006.01)

(52) U.S. Cl.
CPC .......... *G02F 1/092* (2013.01); *A61B 5/14555* (2013.01); *A61B 2562/0233* (2013.01); *A61B 2562/0238* (2013.01)

(58) Field of Classification Search
CPC .... A61B 2562/0238; A61B 2562/0233; G02F 1/092
USPC .................... 600/310, 318, 319, 316, 365
See application file for complete search history.

(56) References Cited

U.S. PATENT DOCUMENTS

| | | | | |
|---|---|---|---|---|
| 5,687,721 | A * | 11/1997 | Kuhls | A61B 5/14558 356/364 |
| 5,788,632 | A * | 8/1998 | Pezzaniti | G01N 21/21 356/368 |
| 6,166,807 | A * | 12/2000 | Kawamura | G01J 4/00 356/364 |
| 6,188,477 | B1 * | 2/2001 | Pu | B82Y 30/00 356/368 |
| 6,246,893 | B1 * | 6/2001 | Gobeli | A61B 5/14558 600/318 |
| 6,370,407 | B1 * | 4/2002 | Kroeger | A61B 5/14558 600/316 |
| 6,466,320 | B1 * | 10/2002 | Kawamura | G01J 4/00 356/364 |
| 6,620,622 | B1 * | 9/2003 | Kawamura | G01N 21/21 250/225 |
| 6,640,116 | B2 * | 10/2003 | Diab | A61B 5/14558 356/367 |
| 6,853,854 | B1 * | 2/2005 | Proniewicz | A61B 5/1455 382/128 |
| 6,885,882 | B2 | 4/2005 | Cote et al. | |
| 6,999,808 | B2 * | 2/2006 | Gobeli | A61B 5/14558 600/316 |
| 7,149,561 | B2 * | 12/2006 | Diab | A61B 5/14558 600/310 |
| RE40,316 | E * | 5/2008 | Gobeli | A61B 5/14558 600/318 |
| 7,801,581 | B2 * | 9/2010 | Diab | A61B 5/14558 356/367 |
| 9,423,635 | B1 * | 8/2016 | Cameron | G02F 1/09 |
| 9,668,678 | B2 * | 6/2017 | Cameron | G02F 1/09 |
| 9,851,293 | B2 * | 12/2017 | Takeda | G01N 21/21 |
| 9,936,874 | B2 * | 4/2018 | Nishizaki | A61B 3/117 |
| 2001/0031914 | A1 * | 10/2001 | Gobeli | A61B 5/14558 600/318 |
| 2002/0049372 | A1 * | 4/2002 | Diab | A61B 5/14558 600/322 |
| 2003/0225321 | A1 * | 12/2003 | Cote | A61B 5/14558 600/318 |
| 2005/0020893 | A1 * | 1/2005 | Diab | A61B 5/14558 600/322 |
| 2005/0154269 | A1 * | 7/2005 | Cameron | A61B 5/14555 600/319 |
| 2007/0083093 | A1 * | 4/2007 | Diab | G01N 21/49 600/310 |
| 2016/0011290 | A1 * | 1/2016 | Iannello | A61B 5/055 600/309 |
| 2016/0324452 | A1 * | 11/2016 | Cameron | G02F 1/09 |

* cited by examiner

FIG 9B Amplifier Circuit Diagram for AMP1 and AMP2
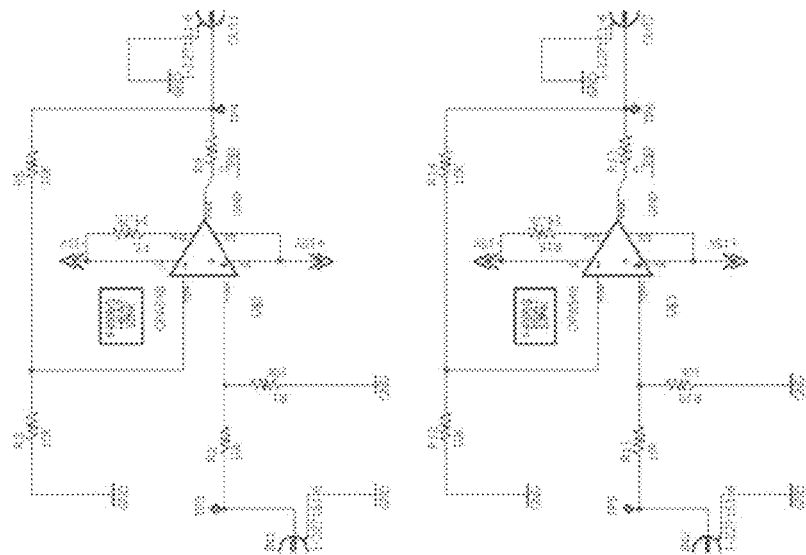
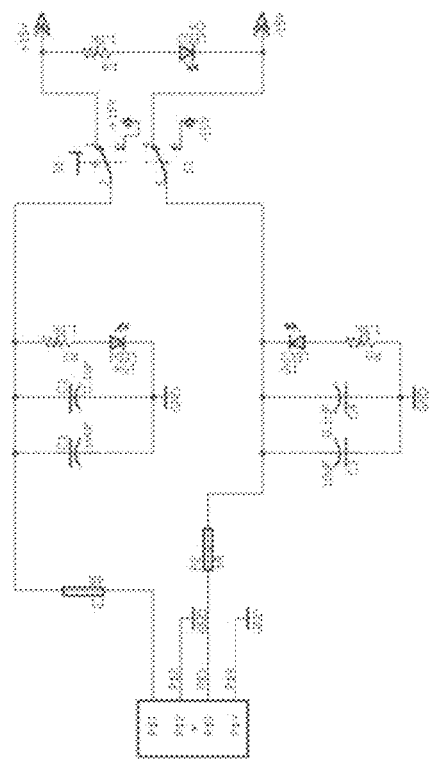

DUAL AMPLITUDE MODULATION AND POLARIZATION FREQUENCY MODULATION AS WELL AS COMPENSATION FOR NONINVASIVE GLUCOSE MONITORING

CROSS-REFERENCE TO RELATED APPLICATION

This application claims priority to U.S. Provisional Patent Application No. 62/366,767 filed on Jul. 26, 2016 and entitled "Dual Amplitude Modulation and Polarization Frequency Modulation as well as Compensation for Noninvasive Glucose Monitoring", the content of which is hereby incorporated by reference.

BACKGROUND

Diabetes is a huge problem in the US and has more than doubled world-wide since 1980 to over 345 million people. Self-monitoring of blood glucose is recommended for diabetic patients as the current standard of care. There is a need by people with Diabetes to monitor glucose noninvasively and avoid the frequent (up to 5 times daily) finger or forearm pricks required today. There is an unmet need for simple, non-invasive self-glucose monitoring devices for people with both Type 1 insulin dependent diabetes and especially for the majority of patients who require less intensive treatment strategies such as those with controlled type 2 diabetes due to life-style modification, oral agent therapy or simple combination oral agent/basal insulin therapy. An equal number of individuals with impaired glucose tolerance and pre-diabetes would benefit from a non-invasive monitoring method to assess their own glucose several times weekly or monthly to detect disease progression. There are also a significant number of patients for whom there is a need for simple non-invasive monitoring for a determinate period of time including women with gestational diabetes, who may or may not be taking insulin, patients with insulin resistance due to heart failure and individuals undergoing chemotherapy or transplant anti-rejection therapies. Thus, there is a very large unmet need for simple non-invasive system.

Existing invasive glucose sensors are commonly used to measure the blood-glucose level of individuals with diabetes. Just by way of example, such sensing systems may be utilized by drawing blood and directly sensing the concentration of glucose in the blood. The problem with these types of sensors is that they are painfully invasive, time consuming, raises concerns about blood borne pathogens, can be embarrassing, and especially troublesome for children. Continuous glucose monitoring (CGM) systems are also available but they are indwelling, suffer from many of the same issues as finger stick devices, and additionally require frequent calibration.

An improved alternative to these invasive glucose sensors is an optical glucose sensor, which is noninvasive. Optical glucose sensors are capable of quantitatively determining the concentration of optically active substances in the human body. As understood by those skilled in the art, the plane of polarization of linearly polarized light rotates as it interacts with optically active material, such as glucose.

FIG. 1 illustrates the principle by which the concentration of an optically active material can be measured utilizing an optical sensor. Unpolarized monochromatic light 100 is passed through a vertical polarizer 105. The linearly polarized light 110 exiting the vertical polarizer 105 is subsequently passed through an optically active sample 115, such as a sample containing glucose. The optically active sample rotates the plane of polarization of the linearly polarized light 110 by an angle, $\phi$, which is proportional to the concentration of the optically active sample. The light exiting the optically active sample is passed through a horizontal polarizer 120. The intensity of the light passing through the horizontal polarizer 120 and detected by the light detector 125 is related to the horizontal component of the plane of polarization introduced by the rotation of the vertically polarized light by the optically active sample 115. Therefore, for a fixed path length through the sample chamber the intensity of the light measured by the detector 125 is proportional to the concentration of the optically active sample.

The fluid contained in the anterior chamber of the eye is known as the aqueous humor and is relatively scatter free, making the anterior chamber an ideal sampling point to detect glucose concentrations utilizing an optical sensor. The diffusion or secretion of glucose into the aqueous humor is highly correlated to the amount of glucose found in the blood. More specifically, the aqueous humor fluid yields a glucose content equal to approximately 70% of that found in blood. Thus, an individual's blood glucose concentration can be ascertained by an optical glucose sensor that detects changes in the plane of polarization of linearly polarized light directed through the anterior chamber of the individual's eye. Examples of such optical glucose sensors may be found in U.S. Pat. Nos. 6,885,882 and 5,209,231, which are herein incorporated by reference.

Although the example process illustrated in FIG. 1 is suitable for measuring large concentrations of optically active substances, additional measures must be taken to accurately measure the relatively small physiological concentration of glucose in the aqueous humor. As illustrated in FIG. 2, a polarization modulation device 225 is added to the example system of FIG. 1 to modulate the plane of polarization of linearly polarized light using the Faraday Effect. According to the Faraday Effect, the plane of polarization of light traveling through a magneto-optic material is rotated by an angle proportional to the magnitude of a magnetic field parallel to the propagation direction of the light, the Verdet constant of the magneto-optic material, and the length of the material according to the formula $\beta = vBL$, where $\beta$ is the magnitude of rotation of the plane of polarization, B is the applied magnetic field, v is the Verdet constant of the magneto-optic material, and L is the length of the magneto-optic material.

The induced modulation allows for the detection of the submillidegree rotational changes, in the plane of polarization, in the presence of optically active substances (e.g., glucose) in the aqueous humor. Due to the relatively short path length and small analyte concentrations present in the aqueous humor, detection of changes in the plane of polarization on the order of 0.4 millidegrees are needed to obtain a system sensitivity comparable to current glucose sensing devices. Utilizing the modulation device, the concentration of glucose can be determined based on the difference between the observed intensity of light at light detector 125 and the expected intensity based on the intentionally induced modulation. Therefore, modulation makes it possible to isolate and detect the small variations in the rotation of the plane of polarization caused by the changes in the concentration of glucose present in the aqueous humor. Detection of the small rotational changes in the optical signal due to the presence of glucose is possible through the use of lock-in amplifiers used to detect the modulated signal. This greatly increases the signal to noise ratio through isolating the modulated signal, thereby, reducing the effects of lower frequency sources of noise such as 60 Hz frequencies emitted by light fixtures in the area of the sampling, thereby improving the sensitivity of the system enabling glucose detection by means of coupling polarized light across the anterior chamber of the eye.

Thus, according to the system for optically sensing glucose levels illustrated in FIG. 2, a laser 205 emits light 100 into a vertical polarizer 105. The polarized light 110 then passes through a polarization modulation device 225. The polarization modulation device 225 rotates the plane of polarization at a frequency (f) with a modulation depth of ±β by applying a magnetic field parallel to the direction of propagation of the polarized light 110 through a magneto-optic material. The modulated light 230 then passes through the aqueous humor fluid 235 contained in the anterior chamber of the eye 240, wherein the plane of polarization is further rotated according to the concentration of optically active molecules in the aqueous humor fluid 235, wherein glucose is the primary optically active molecule. The modulated light 230 next passes through a horizontal polarizer 120 in the same manner as described above with respect to FIG. 1. A light detector 125 measures the intensity of the modulated light 230 and converts it into an electrical signal to be analyzed by a processing unit 255, such as a personal computer, in order to determine the concentration of glucose in the aqueous humor.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 9B illustrates an embodiment depicted three circuits that are included in each of AMP1 and AMP2 in FIG. 9A.

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

While these optical glucose sensors (mentioned above) are an improvement over invasive glucose sensors, Applicant determined problems remain. For example, to accurately measure glucose concentrations in the aqueous humor, optical glucose sensors require polarization modulation mechanisms capable of high modulation frequencies at increased magnetic field strengths. However, existing optical glucose sensors utilize polarization modulation mechanisms based on air gapped solenoid devices 225, which are fraught with problems of their own.

Figure 3:
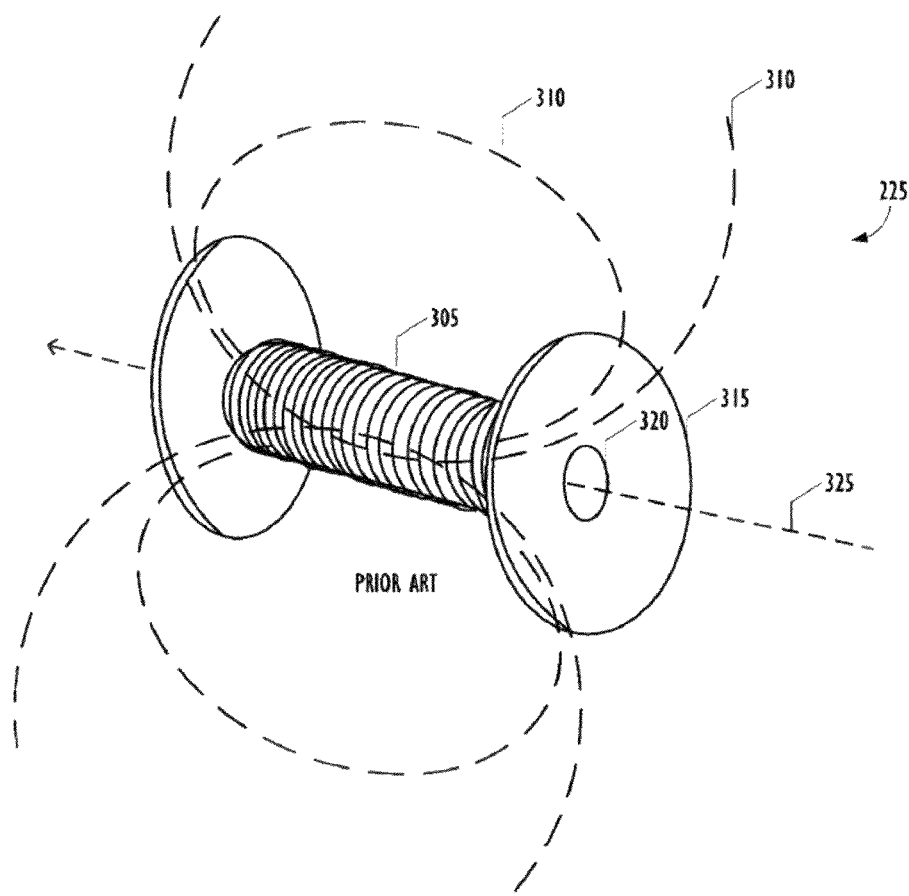
FIG. 3 is a perspective view of an existing air gapped solenoid based polarization modulation device typically utilized in existing optical glucose sensing systems.

Referring to FIG. 3, a typical air gapped solenoid polarization modulation device, commonly referred to as a Faraday rotator, 225 is illustrated. To produce magnetic fields 310 in an air gapped solenoid 225, a conductor 305 is wrapped around a bobbin 315 with an air gap 320 in the center. An optically transparent magneto-optic material with a high Verdet constant is placed within the air gap 320, and, by applying a current to the conductor 305, a magnetic field 310 is produced parallel to the propagation direction of linearly polarized light 325. As noted above, according to the Faraday Effect, this magnetic field 310 rotates the plane of polarization of linearly polarized light 325 passing through the magneto-optic material by a magnitude (β). The magnitude of the generated magnetic field 310 is proportional to the number of turns (N) of the conductor 305, the permeability of free space ($\mu_o$), the applied current, and the overall length of the device.

By applying an alternating current to the conductor 305, an alternating magnetic field 310 is produced. This alternating magnetic field 310 modulates the rotation of the plane of polarization of the linearly polarized light 325 between a lower angle of rotation and an upper angle of rotation. Therefore, to achieve higher modulation frequencies, a higher frequency alternating current must be applied to the conductor 305. At larger modulation frequencies, preferred to obtain accurate real-time measurements of glucose in the aqueous humor (e.g., 100 kHz), Applicant determined many problems, most of which lead to a reduction in the maximum achievable magnetic field, are associated with existing air gapped solenoid devices 225. For instance, with the air gapped design, thousands of turns are needed to produce relatively small magnetic fields (e.g., 17 mT). Due to the large number of turns required, air gapped solenoids are size limited and have large inductances (L) associated with them. This size limitation makes the optical glucose sensor more difficult to use and limits its mobility. Moreover, the large number of turns leads to greater resistivity which creates a need for higher current sources and severely limits the operating frequency range achievable. Higher current sources and greater resistivity, in turn, lead to significantly increased component heat. Additionally, because inductance in the coil 305 increases based on an $N^2$ relationship, there is a need to create RLC circuits to achieve resonance in modulation, even at relatively low frequencies of modulation. These RLC circuits also increase component heat and impact the overall size of optical glucose sensors, adding to the difficulties in use and mobility.

Applicant has therefore determined there is a need in the art to overcome the difficulties associated with current polarimetry based optical glucose sensors by allowing for polarization modulation devices having increased magnetic field strengths at increased modulation frequencies without significant increases in the overall size of the device and without the need for high power current sources or impedance matching circuitry.

To obtain even further increases in frequency embodiments combine the polarization modulation device with modulation of the lasers themselves into a dual modulation scheme that can yield frequencies up to the megahertz range with the polarization modulating devices modulating at sideband frequencies in the hundreds of kilohertz range. The lasers can be amplitude modulated by adjusting their voltage or current at very high megahertz ranges while the polarization is modulated with the modulating devices in the hundreds of kilohertz range.

An embodiment includes an improved modulation approach has been described that includes a polarization modulation device. In one embodiment, the modulation device utilizes a material having a high magnetic permeability to enhance the magnetic field produced through a magneto-optic material. The device is typically comprised of a core material that exhibits high magnetic permeability (e.g., ferrite, Permalloy80, Metglas2605SC, Kool Mu®, molypermalloy powder (MPP), Hiperco, powdered iron, and Mu metal), a transparent rod with a high Verdet constant, and a conductive coil wrapped around the core material. The transparent rod is placed at least partially within a hole that extends through the core so that polarized light may be passed through the transparent rod. Current is supplied to the coil and a magnetic field is propagated through the core, enhancing the magnetic field in the vicinity of the rod. As linearly polarized light is passed through the hole and the rod, an alternating current applied to the coil modulates the rotation of the plane of polarization with a magnitude proportional to the strength of the magnetic field yielding frequencies into the hundreds of kilohertz range. Similarly direct current applied to the other coil provides the constant rotation of the plane of polarization for the compensation. It is to be understood that not all embodiments are limited to the above embodiment and other embodiments for modulating the magnetic field can be modulated are envisioned including a piezo-controlled device attached to a high field generating constant magnetic field magnet, a magnetic core inserted into a second magnetic high permeability core material and the inner core position is adjusted varying the generated magnetic field in the design with respect to the varying high permeability material near the optical crystal, use of a thin layer of high permeability material that allows for optical light polarization state to be rotated after passing through the thin material based on changes in the magnetic properties of the thin piece of material when a voltage in applied to the material, and employing additional optical rotatory components such as the use of Ferro fluid compositions that when a voltage is applied rotate the polarization rotation angle of the optical source.

Moreover, each of these polarization modulation devices can be heterodyned with the lasers in the system to enhance the frequency even further and allow modulation into the megahertz range.

Figure 4A:
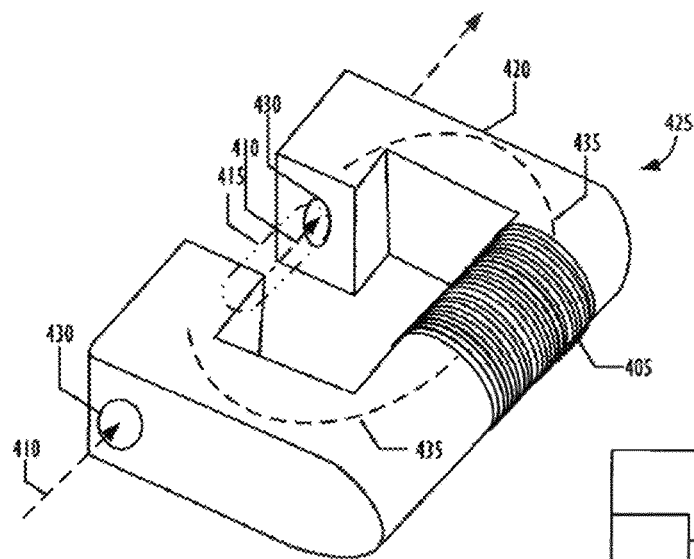
FIG. 4A is a perspective view of one embodiment of an improved polarization modulation device in accordance with one embodiment of the disclosure showing one coil for modulation.
Figure 4B:
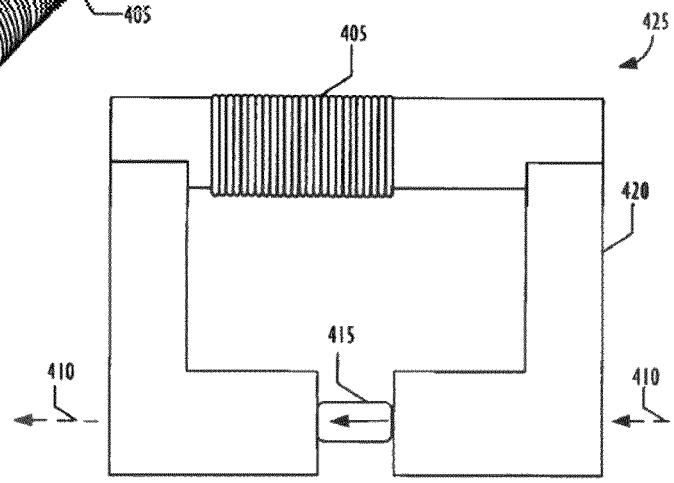
FIG. 4B is a top view of an improved polarization modulation device in accordance with one embodiment of the disclosure showing one coil for modulation.
Figure 4C:
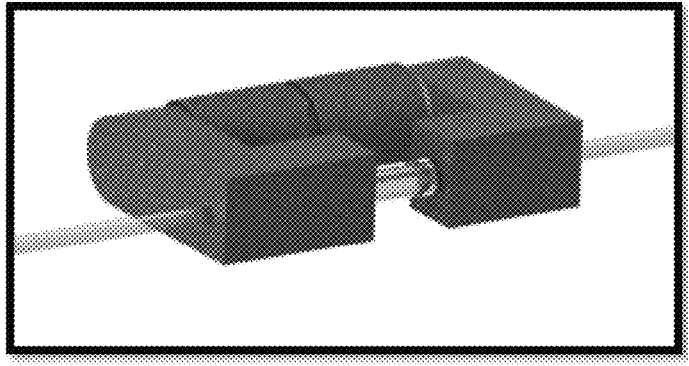
FIG. 4C is a perspective view of one embodiment of an improved polarization modulation device showing two coils, one for modulation and one for feedback to null the signal.
Figure 4D:
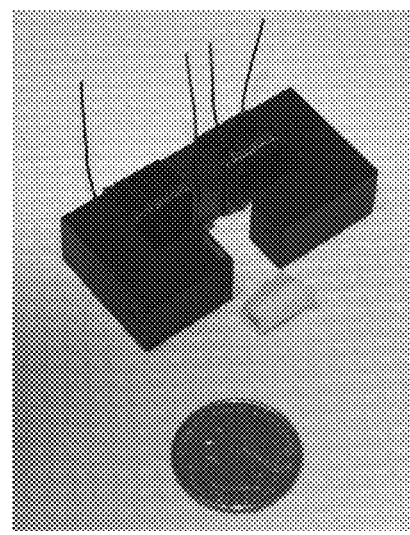
FIG. 4D is a picture of one embodiment of an improved polarization modulation device showing the two coils, one for modulation and one for feedback to null the signal.

Referring to FIG. 4A and FIG. 4B, detailed views of an improved polarization modulation device 425 are depicted. The polarization modulation device comprises a high magnetic permeability core 420 composed of a material that exhibits high magnetic permeability (e.g., ferrite, Permalloy80, Metglas2605SC, Kool Mu®, molypermalloy powder (MPP), Hiperco, powdered iron, and Mu metal). A conductor 405 is wrapped around a portion of the core 420, creating a coil around the core 420. Although the depicted embodiment illustrates a single coil, in an alternate embodiment shown in FIG. 4C and FIG. 4D, two separate coils (e.g., a DC coil and an AC coil) can be wound on the same core 420. In such an embodiment, the polarization modulation device 425 can be used to both modulate the polarization (AC) and compensate the polarization (DC) via one device. This functionality isn't easily achievable with current air gapped solenoid designs 225. Specifically, the AC coil provides the modulation while the DC coil provides feedback (or rather compensation) to the system to null out the rotational signal from the analyte (i.e., glucose). The AC signal modulates the polarization and without analyte (i.e. without glucose) the detector reads a signal that is at twice the modulation frequency of input because of the crossed polarizers. In the presence of the analyte the polarization vector is rotated causing the AC signal to produce a fundamental frequency (i.e., the original modulation frequency). The DC voltage imparted on the second coil is used to offset the polarization rotation from the analyte and drive the AC original modulation frequency signal back to null. This DC voltage is proportional to the rotation and hence concentration of the analyte. Thus, the DC coil provides a mechanism for not only yielding a signal proportional to the rotation and hence concentration of the analyte but provides for more stability since it is used to produce a closed-loop system, which is known to be more stable.

A magneto-optic material 415 with a high Verdet constant is placed in an air gap in the core 420 with the facets of the magneto-optic material 415 aligned with a through hole 430 extending through the core 420. Although in the depicted embodiment the magneto-optic material 415 is aligned with the core 420 such that a through hole 430 is necessary to allow polarized light 410 to be directed through the magneto-optic material 415, in other embodiments, the magneto-optic material may be placed within or near the air gap in a manner in which the through hole 430 is not necessary. For example, in one embodiment, the magneto-optic material 415 may be placed at a 45 degree angle with respect the sides of the air gap such that light can be directed through the magneto-optic material without being obstructed by the core 420. In another embodiment, the magneto-optic material may be positioned just outside of the air gap such that light can be directed through the magneto-optic material without being obstructed by the core 420.

In one embodiment, the magneto-optic material 415 is a terbium-gallium-garnet (TGG) crystal. As is known in the art, TGG crystals are one of the highest Verdet constant magneto-optic materials commercially available, making them ideal for use with the polarization modulation device 425. Consequently, Faraday rotations of significant angles can be achieved by using TGG crystals. However, the magneto-optic material 415 may be composed of any suitable material selected to meet the desired operating characteristics of the device for a particular task. The length of the magnetooptic material can be selected to optimize the uniformity of the magnetic field in the air gap. In one embodiment, however, the magneto-optic material may range from 1-5 mm in diameter and from 0.5-15 mm in length.

As current is supplied to the coil 405, a magnetic field 435 is produced in the core 420 according to the equation $$B = \frac{Ni}{A_{gap}R_{eq}},$$

where B is me generated magnetic field, N is the number of turns of the conductor 405 about the core 420, i is the current applied through the conductor 405, $A_{gap}$ is the area of the air gap, and $R_{eq}$ is the equivalent reluctance of the core 420. Note that equivalent reluctance can be further expanded as follows:

$$B = \frac{Ni}{A_{gap}} * \frac{1}{\left(\frac{l_{core}}{\mu_r\mu_0 A_{core}} + \frac{l_{gap}}{\mu_0 A_{gap}}\right)}$$

where B is magnetic field, $A_{gap}$ and $A_{core}$ are the areas of the air gap and core respectively, i is the current, N is the number of turns of wire, $\mu_r$ is permeability of the core, $l_{gap}$ and $l_{core}$ are the lengths of the core and length of the air gap, and $\mu_0$ is the permeability in a vacuum.

Due to the high magnetic permeability of the core 420, the magnetic field 435 propagates through the core 420 and creates a relatively uniform field across the air gap and magneto-optic material 415. As linearly polarized light 410 is passed through the through hole 430 and the magneto-optic material 415, the plane of polarization is rotated with a magnitude (β) proportional to the strength of the magnetic field 435 and the length of the magneto-optic material 415. As such, excitation of the coil 405 with an alternating current produces an alternating magnetic field that allows for modulation of the rotation of the plane of polarization between a lower angle of rotation and an upper angle of rotation at a desired frequency.

As illustrated in the example embodiments described below, various properties of the improved polarization modulation device can be selected to optimize the modulating characteristics for a particular task. For example, the number of turns of the conductor 405 around the core 420, the size of the conductor 405 and core 420, the length of the air gap in the core 420, the size of the through hole 430, and the material of the conductor 405 and the core 420 each impact the produced magnetic field (and therefore the magnitude of the rotation of the plane of polarization) at a particular frequency. Accordingly, the desired operating characteristics of the improved polarization modulation device for a particular task will dictate the specific design of the device.

Because the improved polarization modulation device 425 utilizes a high magnetic permeability material 420, which can increase the generated magnetic field in the vicinity of the magneto-optic material 415 by several orders of magnitude, the device is capable of achieving higher modulation frequencies at increased magnetic field strengths without significant increases in the overall size of the device as compared to existing air gapped solenoid polarization modulation devices 225. The improved design also allows for modulation of the rotation of the plane of polarization without the need for high power current sources or impedance matching circuitry. The experimental data illustrated in Table 1 and FIGS. 5-7 demonstrate these improved capabilities.

TABLE 1

RLC Measurements of Faraday Modulation Devices

| Frequency (kHz) | 324 Turn Coil | | | 91 Turn Coil | | | 3364 Turn Coil | | |
|---|---|---|---|---|---|---|---|---|---|
| | Resistance (kΩ) | Inductance (mH) | Q | Resistance (kΩ) | Inductance (mH) | Q | Resistance (kΩ) | Inductance (mH) | Q |
| DC | 0.0080 | — | 1 | 0.0016 | — | 1 | 0.076 | — | 1 |
| 0.1 | 0.03814 | 15.23 | 2.68 | 0.001654 | 1.292 | 1.49 | 0.2 | 150.52 | 1.39 |
| 0.12 | 0.05437 | 15.245 | 3.21 | 0.002105 | 1.29 | 2.2 | 0.258 | 151.21 | 1.67 |
| 1 | 3.717 | 15.2 | 26.6 | 0.102 | 1.2914 | 8.7 | 13.403 | 151.21 | 13.5 |
| 10 | 25.9 | 15.518 | 62.9 | 7.05 | 1.2925 | 8.6 | 2362 | 154.27 | 65.1 |

Table 1 illustrates RLC measurements for two ferrite core polarization modulation devices 425 in accordance with an embodiment of the disclosure. For comparison, corresponding RLC measurements for a commonly used 3364 turn air gapped solenoid modulation device 225 are shown. In a first embodiment according to the disclosure, a ferrite core was wrapped with a 324 turn coil of 25 AWG wire. In a second embodiment, a ferrite core was wrapped with a 91 turn coil of 25 AWG wire. Using an RLC meter, inductance, capacitance, resistance, and Q values were measured for DC currents and AC currents at 100 Hz, 120 Hz, 1 kHz, and 10 kHz for each of the devices. As evident from the data recorded in Table 1, the values of inductance and resistance for each of the 324 turn coil and 91 turn coil polarization modulation devices 425 are significantly lower than that of the existing air gapped solenoid modulation device 225, while the Q factor values are comparable. The reduction in AC resistance, shown in the new polarization modulation devices 425, is essential for the generation of AC magnetic fields at higher frequencies (>5 kHz).

In addition to the improvements illustrated above in Table 1, FIGS. 5A and 5B illustrate that each of the 324 turn coil and 91 turn coil polarization modulation devices 425 in accordance with the disclosure is indeed capable of rotating the plane of polarization of linearly polarized light 410 by an amount similar to that achieved using an existing air gapped solenoid device 225. While the DC currents required to achieve these rotations are higher than those required to achieve the same magnitude of rotation using an existing air gapped solenoid device 225, the decreased resistance of the improved device 425 enables rotations of magnitudes similar to existing air gapped solenoid devices 225 at a comparable power. The depicted charts illustrate the rotation of the plane of polarization, as measured by a commercially available polarimeter, for currents ranging from 0-1.05 A supplied from a DC power supply to both the 324 turn coil and 91 turn coil polarization modulation devices 425. As illustrated in the charts, for both the 324 turn coil and 91 turn coil embodiments, the rotation of the plane of polarization increases linearly with increased current supplied to the modulation devices 425. To account for possible hysteresis effects, two runs were conducted for each of the 324 turn coil device and the 91 turn coil device. For the first run, current was sequentially increased from 0-1.05 A, and, for the second run, current was sequentially decreased from 1.05-0 A. These charts illustrate that, despite having far fewer turns as compared to the air gapped solenoid device 225, concentration of the generated magnetic field 435 through the magneto-optic material 415 by the high magnetic permeability material 420 enables the improved device 425 to achieve significant rotations of the plane of polarization of linearly polarized light directed through the magneto-optic material 415.

Figure 5A:
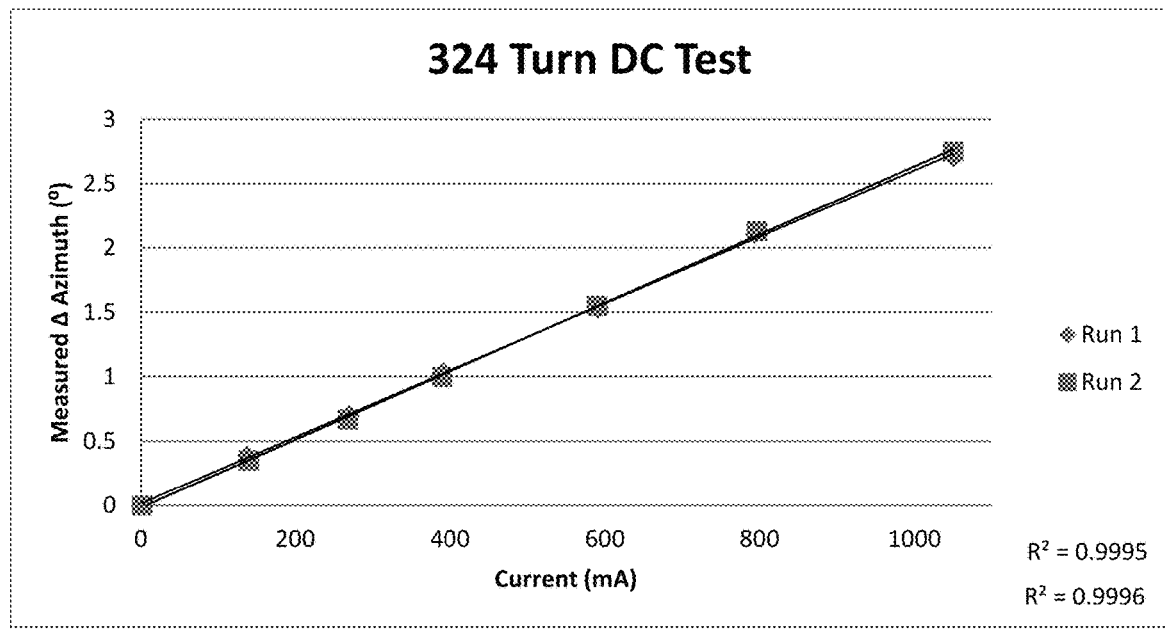
FIGS. 5A-5B illustrate the achievable azimuthal rotation of the plane of polarization of linearly polarized light in accordance with an embodiment of the present invention utilizing a 324 turn coil and a 91 turn coil, respectively.
Figure 5B:
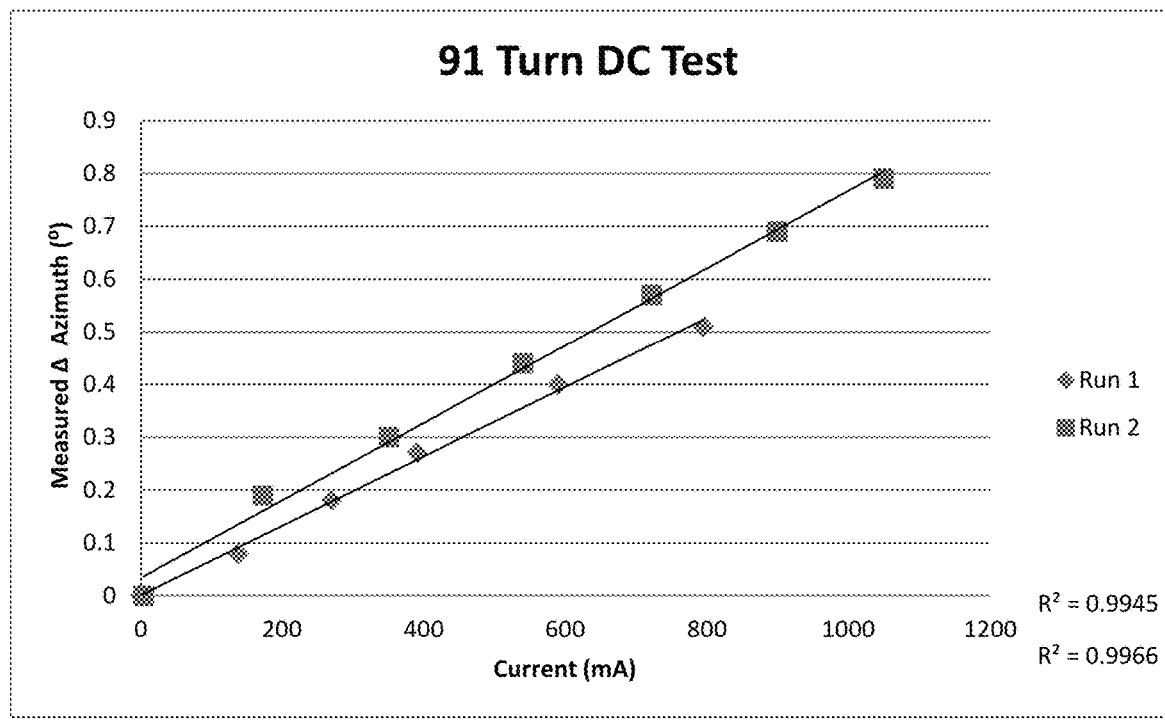
Figure 6A:
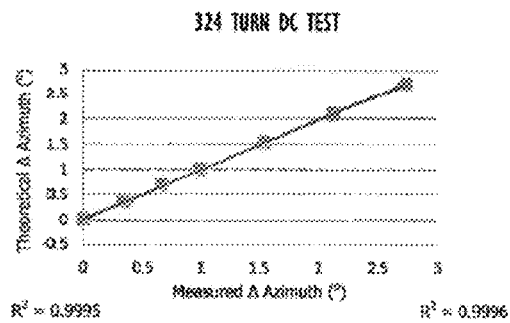
FIGS. 6A-6B illustrate a comparison of the observed azimuthal rotation of the plane of polarization by the 324 turn coil and 91 turn coil devices of FIGS. 5A and 5B with the calculated theoretical rotation of such devices.
Figure 6B:
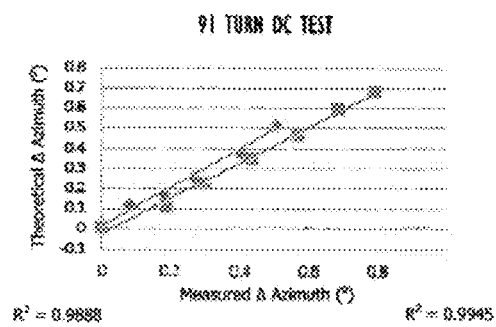

Referring to FIGS. 6A and 6B, the observed rotations of the plane of polarization for the 324 turn coil and 91 turn coil polarization modulation devices 425 (as illustrated in FIGS. 5A and 5B) are compared to theoretical calculations for these devices derived using the variables described above (see discussions regarding Faraday Effect and determination of B-magnetic field). As illustrated in FIGS. 6A and 6B, the measured values correspond very closely to the calculated theoretical values with a coefficient of determination ($R^2$) of 0.9996 for the 324 turn DC test and 0.9945 for the 91 turn DC test. Because the observed values correspond closely to the calculated values, the calculations can be used to optimize modulation devices 425 that achieve a maximum rotation of the plane of polarization with minimum power requirements at desired frequencies.

Figure 7:
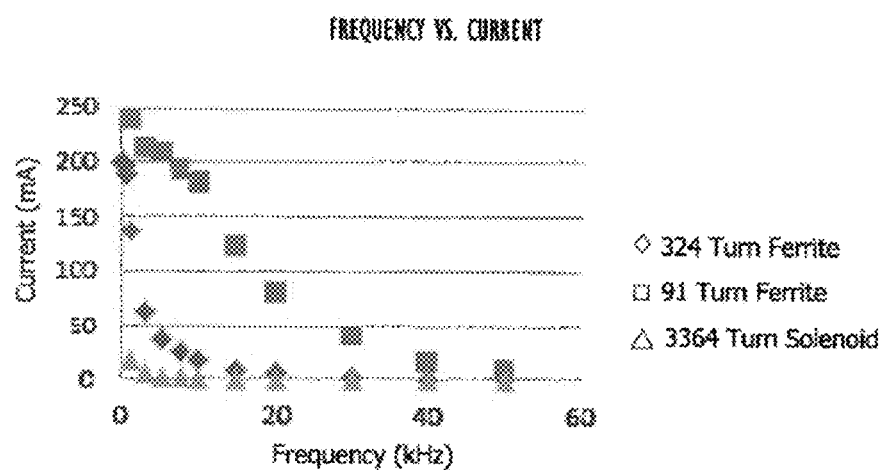
FIG. 7 illustrates a comparison of the effect of increased frequency on the ability to deliver current to the coil of polarization modulation devices for the 91 turn coil and 324 turn coil devices as well as for an existing air gapped solenoid device.

Referring to FIG. 7, the effect of increased frequency on the ability to pass a current through each of the above-described polarization modulation devices is depicted. As is illustrated, the increased impedance of the air gapped solenoid modulation device 225 (and to a lesser degree the 324 turn coil device) with increased frequency rapidly diminishes the ability to deliver current through the coil of the device. Therefore, because the generated magnetic field (and the rotation of the plane of polarization) is proportional to the current applied to the coil, the air gapped solenoid device 225 is incapable of generating a magnetic field capable of significantly rotating the plane of polarization at increased frequencies. Due to the high number of turns required to achieve the desired rotation in existing air gapped solenoid devices 225 and the short path length over which these turns are applied, there has to be a large number of layers. As the number of layers increases, the AC resistance increases exponentially. This is the reason impedance matching is needed for the air gapped solenoid technique. On the other hand, although the 324 turn coil and 91 turn coil modulation devices 425 in accordance with this disclosure require a higher initial current to achieve the same rotation of the plane of polarization as the air gapped solenoid modulation device 225, the lower impedance of these devices as compared to the air gapped solenoid device 225 (especially at increased frequencies) allows the improved devices 425 to achieve similar rotations to the air gapped solenoid device 225 at similar power requirements and to achieve higher frequency modulation of the rotation of the plane of polarization without impedance matching circuitry. Thus, by utilizing a high magnetic permeability material 420 to concentrate a generated magnetic field 435 in the area of a magneto-optic material 415, the improved polarization modulation device 425 allows for larger rotations of the plane of polarization of linearly polarized light 410 at increased frequencies with decreased device sizes as compared to existing polarization modulation devices 225.

Figure 8:
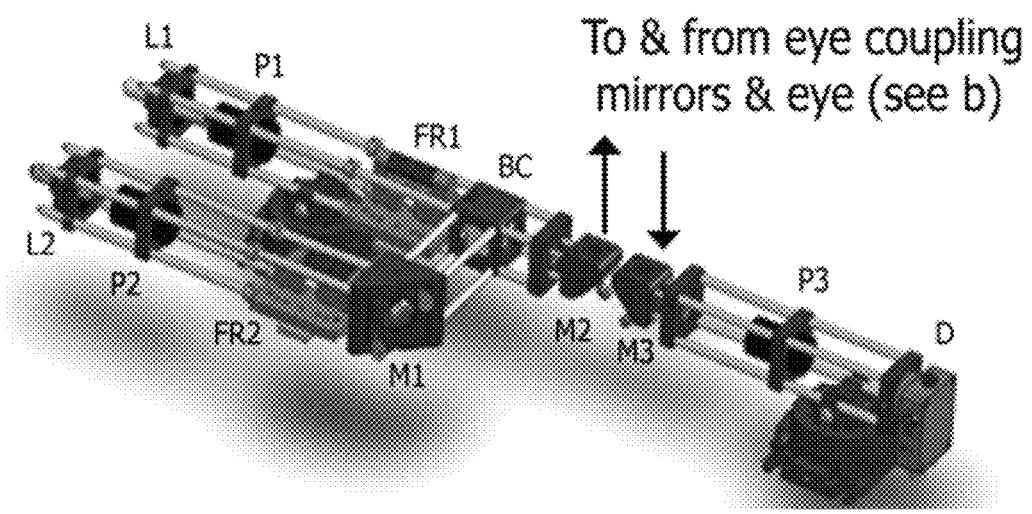
FIG. 8 illustrates one embodiment of the system that includes the lasers heterodyned with the polarization modulators to enhance the frequency of modulation even further into the megahertz range.

One embodiment of the optical setup is illustrated in FIG. 8. Two optical sources used in the design, L1 and L2, are the smaller footprint and longer wavelength laser diodes since they offer temperature control, can be used as one mechanism to enhance specificity by overcoming time varying corneal birefringence, and can provide amplitude modulation up to the megahertz range using either current or voltage variation to drive the laser, if a dual modulation approach is desired. The laser diodes are followed by Glan-Thompson linear polarizers, P1 and P2, that provide strong horizontal linearly polarized states. The individual beams pass through the polarization modulation devices, FR1 and FR2, that operate as both modulators and rotational compensators in order to achieve the AC modulation in the hundreds of kilohertz range and DC closed-loop feedback control. After single or dual modulation from the polarization modulating devices and the two lasers, the two beams are overlaid on top of each other using a beam-splitter/combiner, BC. The combined light beams are passed through the adjustable mirror, M2, through the eye at a glancing angle, and directed and collimated by a set of concave mirrors, M3. The beams, after collimation, are coupled through a linear polarizer, P3, which is positioned perpendicularly to the initial polarizers to act as an analyzer to the optical beams. The beams are coupled to the detector, D, and converted into electronic signals using a photodiode.

Figure 1:
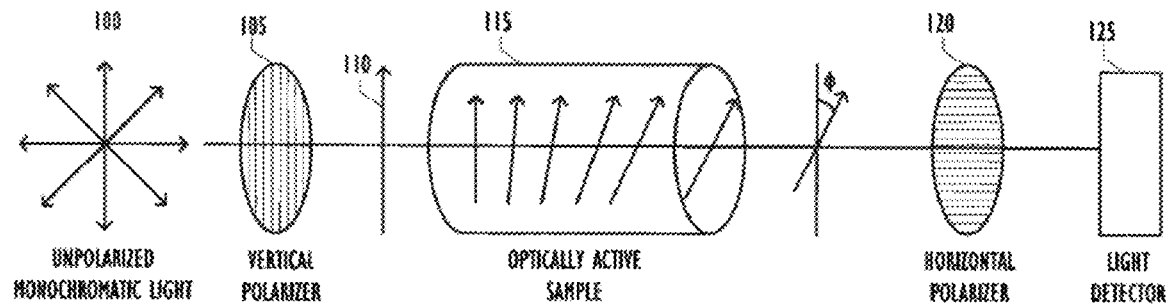
FIG. 1 is a block diagram illustrating a fundamental approach to detect the concentration of an optically active sample based on the rotation of the plane of polarization of linearly polarized light passed through the sample.
Figure 2:
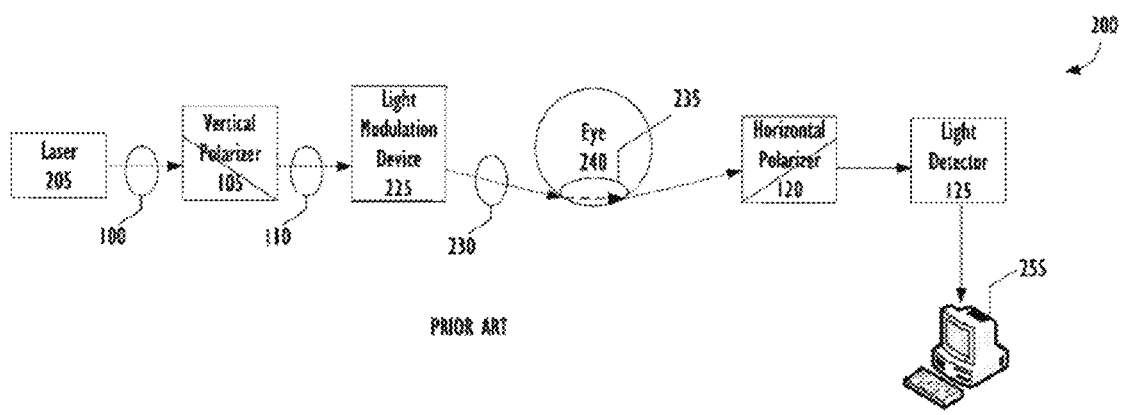
FIG. 2 is a block diagram of an optical glucose sensor utilizing a magneto-optic polarization modulation device.

Although modulation (see discussion above regarding Faraday Effect) provides sensitivity in the system, the cornea of the eye produces birefringence. In particular, as the cornea moves it produces time varying birefringence, which is a type of noise that provides a loss of specificity that Applicant determined cannot be compensated using the single wavelength system of FIG. 2. Therefore, an embodiment includes a method of obtaining both the specificity and sensitivity using the dual wavelength dual modulation system of FIG. 8. Fundamentally, the two wavelengths can be combined in a manner that removes the time varying corneal birefringence noise and provides better specificity.

Figure 9A:
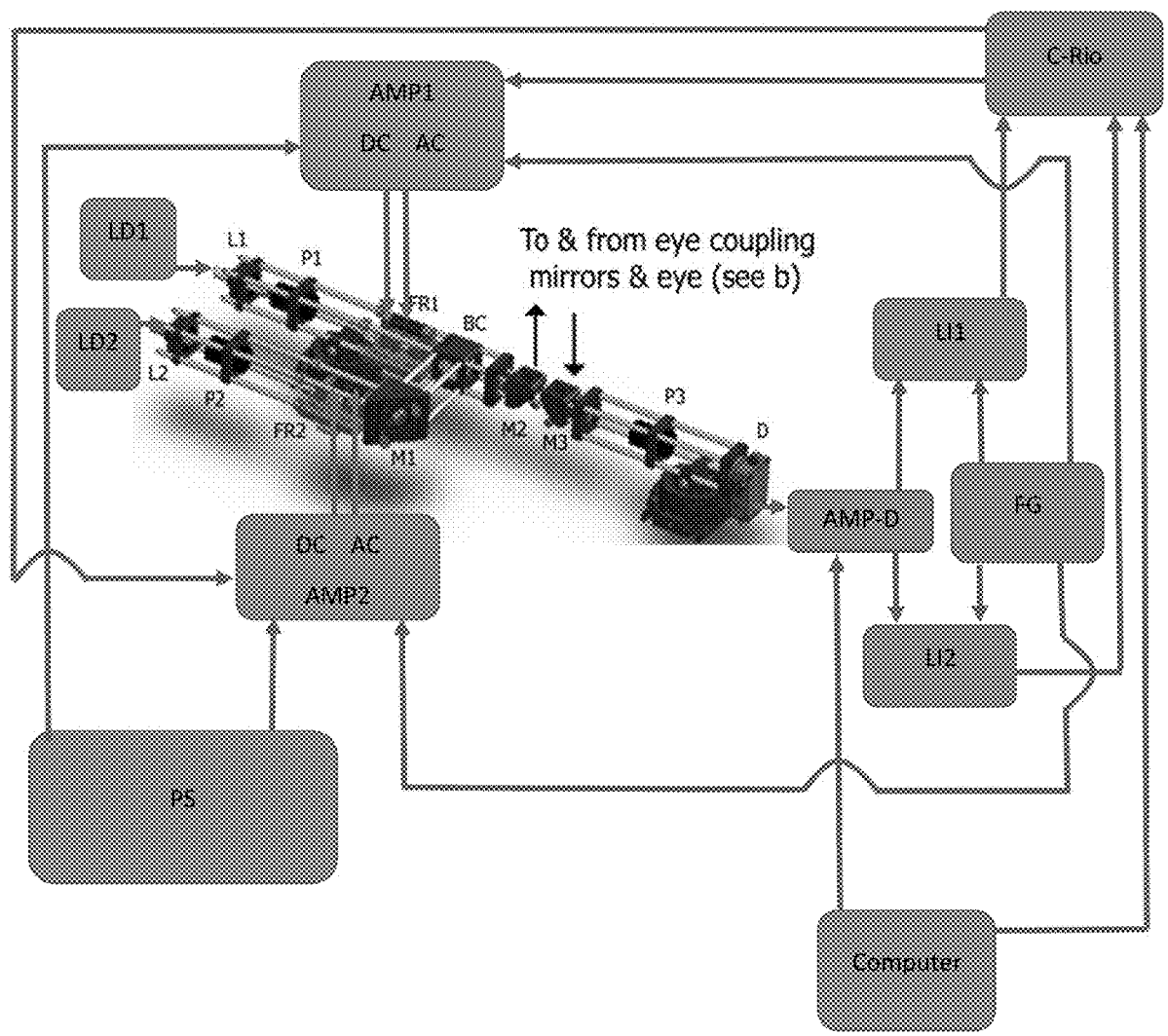
FIG. 9A illustrates one embodiment of the system that includes the lasers heterodyned with the polarization modulators to enhance the frequency of modulation even further into the megahertz range.

As depicted in FIG. 9A the electronic signal from the detector D passes through a wide-bandwidth current amplifier and with noise reduction, AMP-D. The signal is then split and sent to two lock-in amplifiers, LI1 and LI2. The lock-in amplification can be accomplished using two high precision balanced modulator chips such as AD 630 chips that are used with signal processing applications including balanced modulation and demodulation, synchronous detection, phase-sensitive detection, quadrature detection, square wave multiplication, and lock-in amplification. To act as lock-in amplifiers they are coupled with low pass filters in which each chip will lock into the respective frequency (representative of each wavelength) in order to minimize the noise from outside the frequency band of interest and to replace the current bulky commercial lock-in amplifier devices. The reference signals to the two lock-ins are driven by a dual frequency function generator, FG. The electronic outputs of the two lock-in chips will produce DC signals which serve as inputs to the compact rio, C-Rio, which is controlled by the lap-top computer running a PID controller. The outputs of the C-Rio are proportional to the glucose concentration and are thus recorded and used to drive the DC component of the amplifiers, AMP1 and AMP2, and the output of the amplifiers drive the DC coils on the two polarization rotators, FR1 and FR2. The AC component of the two amplifiers, AMP1 and AMP2, are driven by the dual frequency function generator, FG, and the AC output of these two amplifiers drive the AC coils on the faraday rotators, FR1 and FR2.

The amplifier boards, AMP1 and AMP2, are depicted in board circuit diagram is shown in FIG. 9B. In an embodiment each of AMP1 and AMP2 include the three circuits shown in FIG. 9B. The amplifier boards AMP1 and AMP2 are powered using a separate power supply, PS. The DC data that drives the two amplifiers AMP1 and AMP2 is collected in the computer and processed using algorithms that provide a real-time glucose response, essential for overcoming time varying corneal birefringence & providing a user friendly device with minimal data collection time. In this embodiment, advantages are achieved through an improved optical modulation design utilizing polarization modulators, FR1 and FR2, and can be further enhanced using dual modulation that includes voltage or current driven modulating laser drivers, LD1 and LD2. Since we can heterodyne the polarization modulation with lasers amplitude modulating we gain the ability to modulate up to the megahertz range and the polarization modulation devices modulating at side band frequencies achievable up to hundreds of KHz. In an embodiment, the circuits of FIG. 9B are located on two parts of the same board. In other words, AMP1 and AMP2 are exactly the same in an embodiment and both of them have these same circuits on them but are just connected to the two different DC sources from the c-Rio and two different AC signals from the dual function generator on the input and two faraday rotators on the output.

It is to be understood that the present invention is not limited to the above embodiments. For example, the 91 turn and 324 turn coil devices 425 are described only to illustrate improvements over existing polarization modulation devices 225 and are not intended to be limiting in any manner. In addition, the depicted design of the polarization modulation device is not intended to be limiting in any manner. Rather, the polarization modulation device includes any modulation device utilizing a magnetically permeable material to concentrate a generated magnetic field in the vicinity of a magneto-optic material in order to rotate the plane of polarization of light passing through the magneto-optic material.

For example, in another embodiment, the magnetic field can be modulated using a piezo-controlled device attached to a high field generating constant magnetic field magnet. Such a configuration allows for high frequency modulation with significant reduction in the power required to generate the sinusoidal signal at increased frequencies.

In an additional embodiment, a magnetic core of a given permeability is inserted into a second magnetic high permeability shell material in a hole created through the magnetic shell winding arm. The inner core position is adjusted to either fill the shell or be within it in a varying amount allowing for changing the generated magnetic field in the design with respect to the varying high permeability material near the optical crystal.

Another embodiment consists of a very thin layer of high permeability material that allows the optical beam to be transmitted through it without varying the polarization or optical power significantly. Further, it allows for optical light polarization state to be rotated after passing through the thin magnetic material based on changes in the magnetic properties of the thin piece of material when a voltage and/or current is applied to the material.

An additional embodiment employs the use of Ferro fluid compositions that, when a voltage is applied, rotate the polarization angle of the optical source. Specifically, when the optical beam is passed through a medium of Ferro fluid, the fluid is activated by application of a voltage, which then modulates the state of the polarization.

In addition, each of these polarization modulation embodiments can be heterodyned with the lasers to increase the frequency even further and allow modulation into the megahertz range. Heterodyning is used to shift one frequency range of a system to another by combining signals. In the most common application, two signals at frequencies $f_1$ and $f_2$ are mixed, creating two new signals, one at the sum $f_1+f_2$ the two frequencies, and the other at the difference $f_1-f_2$ Moreover, although the polarization modulation device has been described with respect to an optical glucose sensor, it is to be understood that the polarization modulation device is not limited to such use. For example, Faraday rotation spectroscopy is another sensing modality that may benefit from the improved modulation device. In addition, due to the relatively low power requirements of the polarization modulation device, it can be used to switch the state of polarization of light between orthogonal states. Such a device may be beneficial in the design of polarization-based optical switches and active optical isolators. A magneto-optic modulator which can rotate the state of polarization by 90 degrees can also be used for intensity modulation of light in a configuration similar to how Pockel cell is used. Moreover, a magneto-optic modulator may also be used to create a heterodyne light source used in heterodyne interferometry and polarimetry.

Another potential application of the improved device is in the development of active Faraday filters and Voigt filters. Faraday filters are atomic line filters which utilize increased Faraday rotation and anomalous dispersion near a gas's atomic absorption lines. In a Voigt filter, a magnetic field is applied perpendicular to the direction of propagation of light, resulting in the creation of a magnetically induced birefringence.

Figure 10:
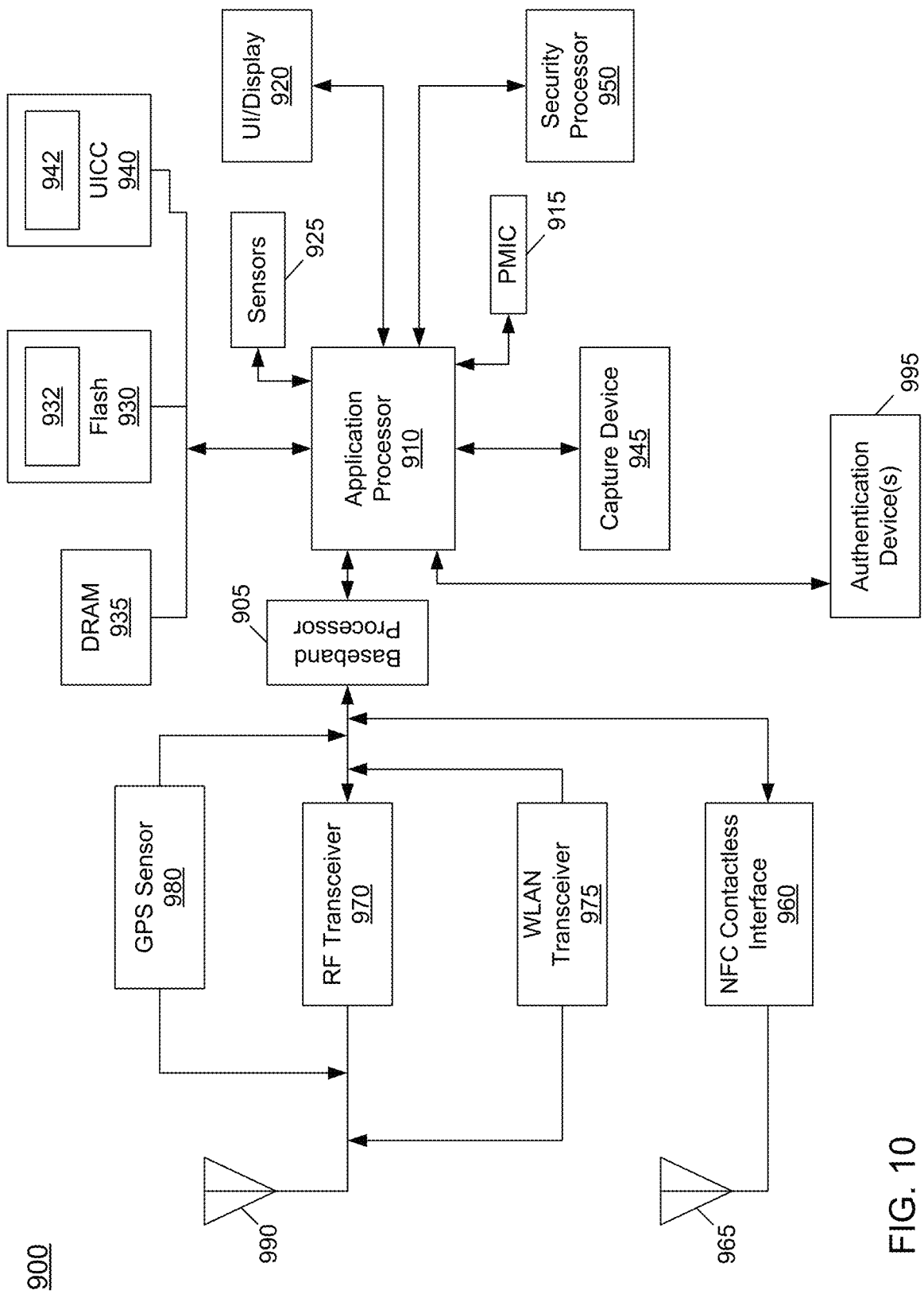
FIGS. 10, 11, 12 include systems with which embodiments may be implemented.

Referring now to FIG. 10, shown is a block diagram of an example system with which embodiments can be used. As seen, system 900 may be a smartphone or other wireless communicator or any other Internet of Things (IoT) device. A baseband processor 905 is configured to perform various signal processing with regard to communication signals to be transmitted from or received by the system. In turn, baseband processor 905 is coupled to an application processor 910, which may be a main CPU of the system to execute an OS and other system software, in addition to user applications such as many well-known social media and multimedia apps. Application processor 910 may further be configured to perform a variety of other computing operations for the device.

In turn, application processor 910 can couple to a user interface/display 920 (e.g., touch screen display). In addition, application processor 910 may couple to a memory system including a non-volatile memory, namely a flash memory 930 and a system memory, namely a DRAM 935. In some embodiments, flash memory 930 may include a secure portion 932 in which secrets and other sensitive information may be stored. As further seen, application processor 910 also couples to a capture device 945 such as one or more image capture devices that can record video and/or still images.

A universal integrated circuit card (UICC) 940 comprises a subscriber identity module, which in some embodiments includes a secure storage 942 to store secure user information. System 900 may further include a security processor 950 (e.g., Trusted Platform Module (TPM)) that may couple to application processor 910. A plurality of sensors 925, including one or more multi-axis accelerometers may couple to application processor 910 to enable input of a variety of sensed information such as motion and other environmental information. In addition, one or more authentication devices 995 may be used to receive, for example, user biometric input for use in authentication operations.

As further illustrated, a near field communication (NFC) contactless interface 960 is provided that communicates in a NFC near field via an NFC antenna 965. While separate antennae are shown, understand that in some implementations one antenna or a different set of antennae may be provided to enable various wireless functionalities.

A power management integrated circuit (PMIC) 915 couples to application processor 910 to perform platform level power management. To this end, PMIC 915 may issue power management requests to application processor 910 to enter certain low power states as desired. Furthermore, based on platform constraints, PMIC 915 may also control the power level of other components of system 900.

To enable communications to be transmitted and received such as in one or more IoT networks, various circuitry may be coupled between baseband processor 905 and an antenna 990. Specifically, a radio frequency (RF) transceiver 970 and a wireless local area network (WLAN) transceiver 975 may be present. In general, RF transceiver 970 may be used to receive and transmit wireless data and calls according to a given wireless communication protocol such as 3G or 4G wireless communication protocol such as in accordance with a code division multiple access (CDMA), global system for mobile communication (GSM), long term evolution (LTE) or other protocol. In addition a GPS sensor 980 may be present, with location information being provided to security processor 950 for use as described herein when context information is to be used in a pairing process. Other wireless communications such as receipt or transmission of radio signals (e.g., AM/FM) and other signals may also be provided. In addition, via WLAN transceiver 975, local wireless communications, such as according to a Bluetooth™ or IEEE 802.11 standard can also be realized.

Figure 11:
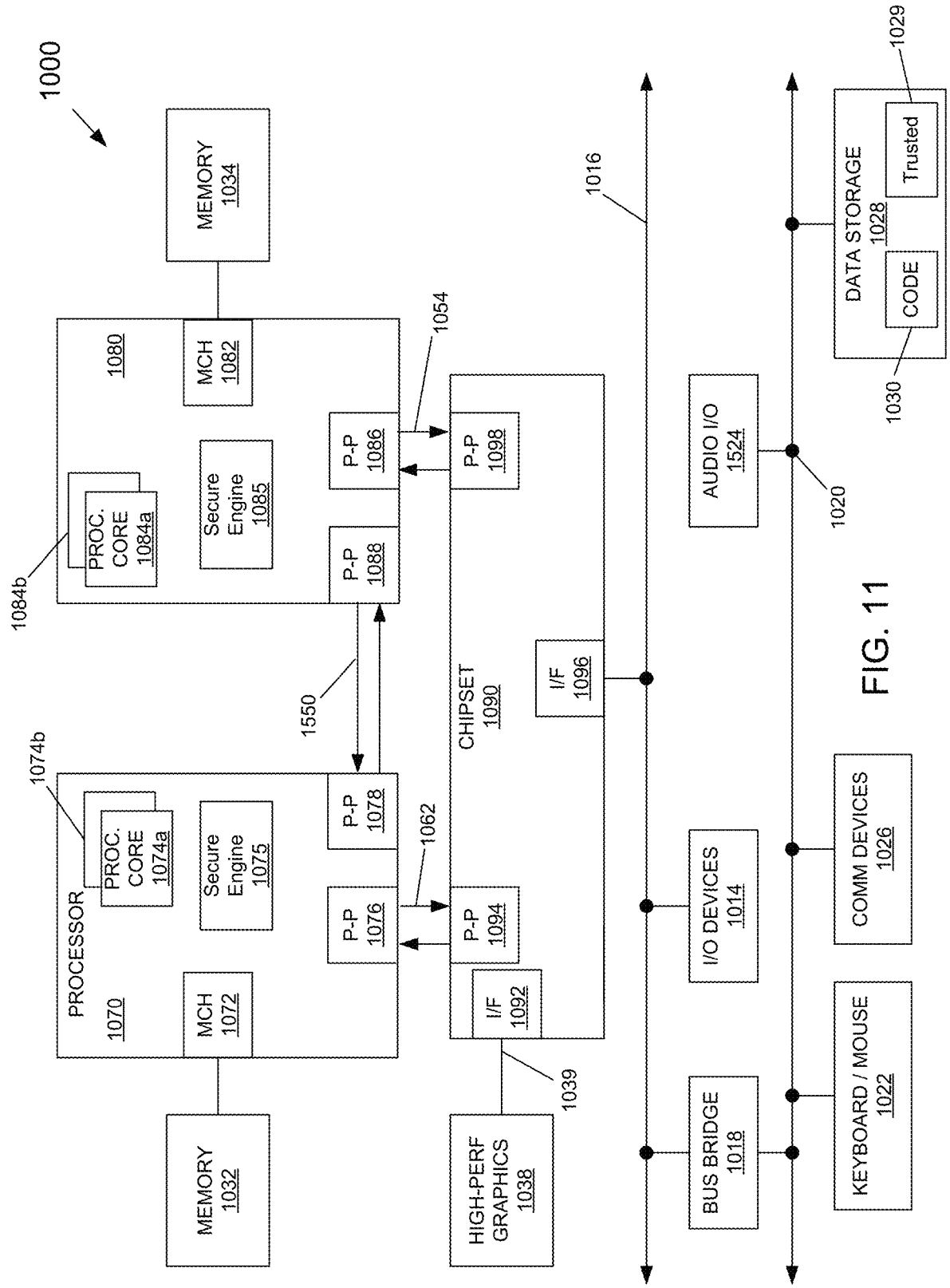

Referring now to FIG. 11, shown is a block diagram of a system in accordance with another embodiment of the present invention. Multiprocessor system 1000 is a point-to-point interconnect system such as a server system, and includes a first processor 1070 and a second processor 1080 coupled via a point-to-point interconnect 1050. Each of processors 1070 and 1080 may be multicore processors such as SoCs, including first and second processor cores (i.e., processor cores 1074*a* and 1074*b* and processor cores 1084*a* and 1084*b*), although potentially many more cores may be present in the processors. In addition, processors 1070 and 1080 each may include a secure engine 1075 and 1085 to perform security operations such as attestations, IoT network onboarding or so forth.

First processor 1070 further includes a memory controller hub (MCH) 1072 and point-to-point (P-P) interfaces 1076 and 1078. Similarly, second processor 1080 includes a MCH 1082 and P-P interfaces 1086 and 1088. MCH's 1072 and 1082 couple the processors to respective memories, namely a memory 1032 and a memory 1034, which may be portions of main memory (e.g., a DRAM) locally attached to the respective processors. First processor 1070 and second processor 1080 may be coupled to a chipset 1090 via P-P interconnects 1052 and 1054, respectively. Chipset 1090 includes P-P interfaces 1094 and 1098.

Furthermore, chipset 1090 includes an interface 1092 to couple chipset 1090 with a high performance graphics engine 1038, by a P-P interconnect 1039. In turn, chipset 1090 may be coupled to a first bus 1016 via an interface 1096. Various input/output (I/O) devices 1014 may be coupled to first bus 1016, along with a bus bridge 1018 which couples first bus 1016 to a second bus 1020. Various devices may be coupled to second bus 1020 including, for example, a keyboard/mouse 1022, communication devices 1026 and a data storage unit 1028 such as a non-volatile storage or other mass storage device. As seen, data storage unit 1028 may include code 1030, in one embodiment. As further seen, data storage unit 1028 also includes a trusted storage 1029 to store sensitive information to be protected. Further, an audio I/O 1024 may be coupled to second bus 1020.

Figure 12:
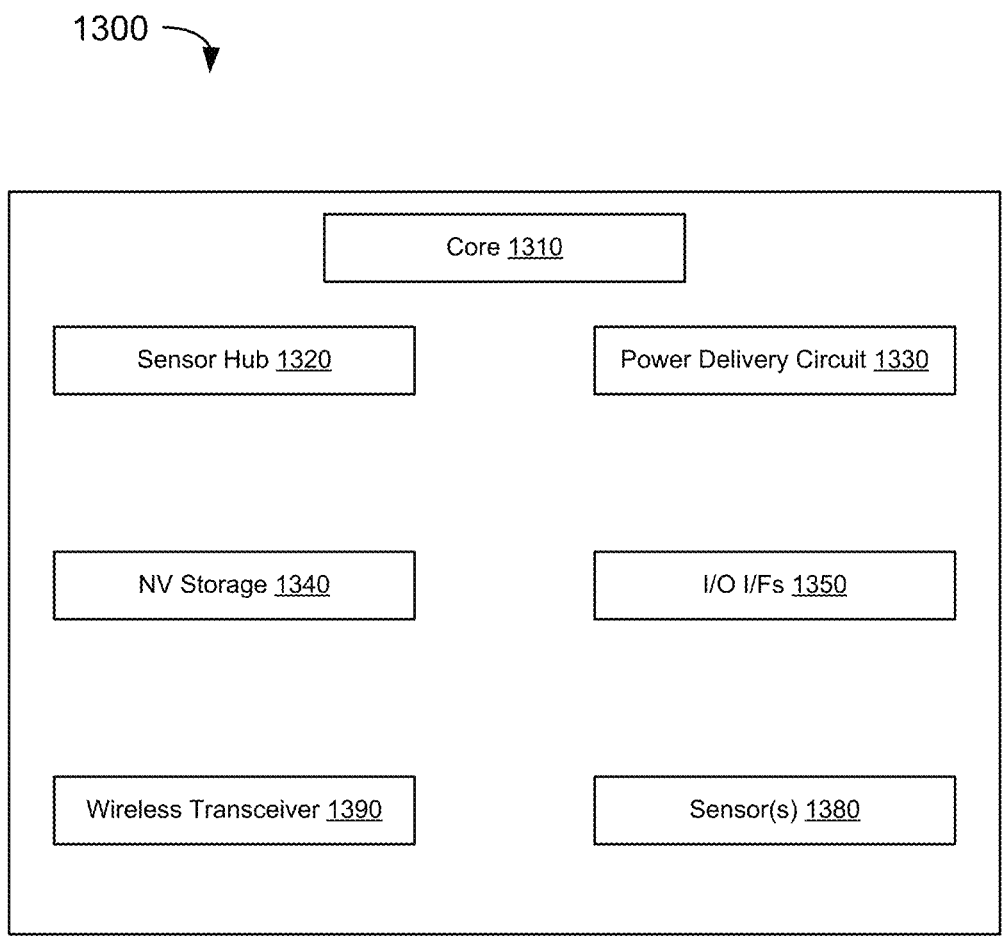

Embodiments may be used in environments where IoT devices may include wearable devices (e.g., spectacles including system shown in, for example, FIG. 8) or other small form factor Internet of Things (IoT) devices. Referring now to FIG. 12, shown is a block diagram of a wearable module 1300 in accordance with another embodiment. In one particular implementation, module 1300 may be an Intel® Curie™ module that includes multiple components adapted within a single small module that can be implemented as all or part of a wearable device. As seen, module 1300 includes a core 1310 (of course in other embodiments more than one core may be present). Such core may be a relatively low complexity in-order core, such as based on an Intel Architecture® Quark™ design. In some embodiments, core 1310 may implement a Trusted Execution Environment (TEE). Core 1310 couples to various components including a sensor hub 1320, which may be configured to interact with a plurality of sensors 1380, such as one or more biometric, motion environmental or other sensors. A power delivery circuit 1330 is present, along with a non-volatile storage 1340. In an embodiment, this circuit may include a rechargeable battery and a recharging circuit, which may in one embodiment receive charging power wirelessly. One or more input/output (IO) interfaces 1350, such as one or more interfaces compatible with one or more of USB/SPI/I2C/GPIO protocols, may be present. In addition, a wireless transceiver 1390, which may be a Bluetooth™ low energy or other short-range wireless transceiver is present to enable wireless communications as described herein. Understand that in different implementations a wearable module can take many other forms. Wearable and/or IoT devices have, in comparison with a typical general purpose CPU or a GPU, a small form factor, low power requirements, limited instruction sets, relatively slow computation throughput, or any of the above.

Embodiments may be used in many different types of systems. For example, in one embodiment a communication device can be arranged to perform the various methods and techniques described herein. Of course, the scope of the present invention is not limited to a communication device, and instead other embodiments can be directed to other types of apparatus for processing instructions, or one or more machine readable media including instructions that in response to being executed on a computing device, cause the device to carry out one or more of the methods and techniques described herein.

Program instructions may be used to cause a general-purpose or special-purpose processing system that is programmed with the instructions to perform the operations described herein. Alternatively, the operations may be performed by specific hardware components that contain hard-wired logic for performing the operations, or by any combination of programmed computer components and custom hardware components. The methods described herein may be provided as (a) a computer program product that may include one or more machine readable media having stored thereon instructions that may be used to program a processing system or other electronic device to perform the methods or (b) at least one storage medium having instructions stored thereon for causing a system to perform the methods. The term "machine readable medium" or "storage medium" used herein shall include any medium that is capable of storing or encoding a sequence of instructions (transitory media, including signals, or non-transitory media) for execution by the machine and that cause the machine to perform any one of the methods described herein. The term "machine readable medium" or "storage medium" shall accordingly include, but not be limited to, memories such as solid-state memories, optical and magnetic disks, read-only memory (ROM), programmable ROM (PROM), erasable PROM (EPROM), electrically EPROM (EEPROM), a disk drive, a floppy disk, a compact disk ROM (CD-ROM), a digital versatile disk (DVD), flash memory, a magneto-optical disk, as well as more exotic mediums such as machine-accessible biological state preserving or signal preserving storage. A medium may include any mechanism for storing, transmitting, or receiving information in a form readable by a machine, and the medium may include a medium through which the program code may pass, such as antennas, optical fibers, communications interfaces, and the like. Program code may be transmitted in the form of packets, serial data, parallel data, and the like, and may be used in a compressed or encrypted format. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

A module as used herein refers to any hardware, software, firmware, or a combination thereof. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term logic includes hardware, such as transistors, registers, or other hardware, such as programmable logic devices. However, in another embodiment, logic also includes software or code integrated with hardware, such as firmware or micro-code.

Example 1 includes a device, comprising: light polarization rotation modulation, light polarization constant rotation, laser amplitude modulation, and heterodyned modulation between the lasers and polarization modulation.

Example 2 includes the device of example 1, wherein the polarization modulation comprises: a magnetically permeable core having an air gap; a magneto-optic material at least partially disposed within the air gap; and one or more conductors wrapped around a portion of the magnetically permeable core, wherein a current passed through the conductor generates a magnetic field that propagates through the magnetically permeable core and rotates a plane of polarization of light directed through the magneto-optic material.

Example 3 includes the device of example 2, wherein the magneto-optic material is terbium-gallium-garnet (TGG) crystal.

Example 4 includes the device of example 3, wherein the TGG crystal is approximately 1 centimeter long.

Example 5 includes the device of example 2, wherein a first one of the one or more conductors carries an alternating current and a second one of the one or more conductors carries a direct current.

Example 6 includes the device of example 5, wherein the alternating current has a frequency between 1 kHZ and 1 MHz.

Example 7 includes the device of example 5, wherein the alternating current generates an alternating magnetic field.

Example 8 includes the device of example 7, wherein the alternating magnetic field modulates the rotation of the plane of polarization of the light between a lower angle of rotation and an upper angle of rotation.

Example 9 includes a system for measuring glucose levels in the aqueous humor of the eye, comprising: a light source configured to generate a light beam; a polarizer configured to linearly polarize the light beam; a polarization modulation device to modulate a rotation of a plane of polarization of the linearly polarized light beam, the polarization modulation device comprising: a magnetically permeable core having an air gap; a magneto-optic material at least partially disposed within the air gap; and one or more conductors wrapped around a portion of the magnetically permeable core, wherein a current passed through the one or more conductors generates a magnetic field that propagates through the magnetically permeable core and rotates the plane of polarization of the linearly polarized light directed through the magneto-optic material generating a modulated light beam; and a detector unit for receiving the modulated light beam after the modulated light beam is passed through the aqueous humor, the detector unit configured detect a change in the plane of polarization of the modulated light beam as a result of a concentration of glucose in the aqueous humor.

Not all embodiments require each of these elements. For example, only the polarization modulation device may be provided in some embodiments. In some embodiments the detector is omitted and a third party may provide such a detector. Also, reciting "a light source" does not mean that embodiments cannot include two, three or more light sources.

Example 10 includes the system of example 9, wherein the magneto-optic material is terbium-gallium-garnet (TGG) crystal.

Example 11 includes the system of example 10, wherein the TGG crystal is approximately 1 centimeter long.

However, in other embodiments the crystal (regardless of what type of crystal is used) is 0.5, 1.5, 2.5 cm or longer.

Example 12 includes the system of example 9, wherein a first one of the one or more conductors carries an alternating current and a second one of the one or more conductors carries a direct current.

Example 13 includes the system of example 12, wherein the alternating current has a frequency between 1 kHZ and 1 MHz.

Example 14 includes the system of example 12, wherein the alternating current generates an alternating magnetic field.

Example 15 includes the system of example 14, wherein the alternating magnetic field modulates the rotation of the plane of polarization of the light between a lower angle of rotation and an upper angle of rotation.

Example 16 includes a method for measuring glucose levels in the aqueous humor of the eye, comprising the steps of: generating a linearly polarized light beam; passing the linearly polarized light beam through a polarization modulation device comprising: a magnetically permeable core; a through hole extending through at least a portion of the magnetically permeable core; a magneto-optic material at least partially disposed within the through hole; and a conductor wrapped around a portion of the magnetically permeable core; passing an alternating current through the conductor to generate an alternating magnetic field that propagates through the magnetically permeable core and modulates a rotation of a plane of polarization of the linearly polarized light passed through the polarization modulation device to generate a modulated light beam; passing the modulated light beam through the aqueous humor; and detecting a change in the plane of polarization of the modulated light beam as a result of a concentration of glucose in the aqueous humor.

Example 17 includes the method of example 16, wherein the magneto-optic material is terbium-gallium-garnet (TGG) crystal.

Example 18 includes the method of example 17, wherein the TGG is approximately 1 centimeter long.

It is to be understood that the above description and examples are intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

What is claimed is:

1. A system to measure glucose levels in an aqueous humor of an eye, the system comprising:
    two light sources to generate two light beams at different wavelengths;
    two polarizers to respectively linearly polarize each of the light beams;
    two polarization modulation modules to respectively modulate the rotation of a plane of polarization of each of the linearly polarized light beams, each of the polarization modulation modules comprising: (a)(i) a magnetically permeable core having an air gap; (a)(ii) a magneto-optic material at least partially disposed within the air gap; and (a)(iii) at least one conductor wrapped around a portion of the magnetically permeable core; and
    a detector module;
    wherein with each polarization modulation module when a current is passed through at least one conductor (b)(i) a magnetic field is generated and propagates through the magnetically permeable core, and (b)(ii) the magnetic field rotates the plane of polarization of the linearly polarized light for the light source, when the linearly polarized light is directed through the magneto-optic material, generating a modulated light beam;
    wherein the detector unit is to (c)(i) receive the modulated light beams after the modulated light beams are passed through the aqueous humor of the eye, and (c)(ii) detect a change in the plane of polarization of each of the modulated light beams in response to a concentration of glucose in the aqueous humor.

2. The system of claim 1, wherein the magneto-optic material includes a terbium-gallium-garnet (TGG) crystal.

3. The system of claim 2, wherein the TGG crystal is approximately 1 centimeter long.

4. The system of claim 3, wherein with each polarization modulation module a first one of the one or more conductors is to carry an alternating current and a second one of the one or more conductors is to carry a direct current.

5. The system of claim 4, wherein the alternating current has a frequency between 1 kHZ and 1 MHz.

6. The system of example 4, wherein the alternating current is to generate an alternating magnetic field.

7. The system of example 6, wherein the alternating magnetic field is to modulate the rotation of the plane of polarization of the light between a lower angle of rotation and an upper angle of rotation.

8. The system of claim 4, wherein the direct current is supplied by a feedback loop to produce a magnetic field that compensates for the rotation from the glucose signal.

9. The system of claim 1 wherein the light sources are modulated at frequencies between 10 KHz to 1 MHz.

10. The system of claim 1 wherein the light sources are heterodyned with the polarization modulation modules.

11. A method of measuring glucose levels in an aqueous humor of an eye comprising:
    generating a linearly polarized light beam;
    passing the linearly polarized light beam through a polarization modulation device comprising: (a)(i) a magnetically permeable core; (a)(ii) an aperture extending through at least a portion of the magnetically permeable core; (a)(iii) a magneto-optic material at least partially disposed within the through hole; and (a)(iv) a conductor wrapped around a portion of the magnetically permeable core;
    passing an alternating current through the conductor to generate an alternating magnetic field that propagates through the magnetically permeable core and modulates a rotation of a plane of polarization of the linearly polarized light passed through the polarization modulation device to generate a modulated light beam;
    passing the modulated light beam through the aqueous humor; and
    detecting a change in the plane of polarization of the modulated light beam in response to a concentration of glucose in the aqueous humor.

12. The method of claim 11, wherein the magneto-optic material is terbium-gallium-garnet (TGG) crystal.

13. The method of claim 12, wherein the TGG is approximately 1 centimeter long.

14. A system to measure glucose levels in an aqueous humor of an eye, the system comprising:
    a light source to generate a light beam;
    a polarizer to linearly polarize the light beam;

a polarization modulation module to modulate a rotation of a plane of polarization of the linearly polarized light beam, the polarization modulation module comprising:
(a)(i) a magnetically permeable core having an air gap;
(a)(ii) a magneto-optic material at least partially disposed within the air gap; and (a)(iii) at least one conductor wrapped around a portion of the magnetically permeable core; and a detector module;

wherein when a current is passed through the at least one conductor (b)(i) a magnetic field is generated and propagates through the magnetically permeable core, and (b)(ii) the magnetic field rotates the plane of polarization of the linearly polarized light, when the linearly polarized light is directed through the magneto-optic material, generating a modulated light beam;

wherein the detector unit is to (c)(i) receive the modulated light beam after the modulated light beam is passed through the aqueous humor, and (c)(ii) detect a change in the plane of polarization of the modulated light beam in response to a concentration of glucose in the aqueous humor.

15. The system of claim 14, wherein the magneto-optic material includes a terbium-gallium-garnet (TGG) crystal.

16. The system of claim 15, wherein the TGG crystal is approximately 1 centimeter long.

17. The system of claim 16, wherein a first one of the one or more conductors is to carry an alternating current and a second one of the one or more conductors is to carry a direct current.

18. The system of claim 17, wherein the alternating current has a frequency between 1 kHZ and 1 MHz.

19. The system of example 17, wherein the alternating current is to generate an alternating magnetic field.

20. The system of example 19, wherein the alternating magnetic field is to modulate the rotation of the plane of polarization of the light between a lower angle of rotation and an upper angle of rotation.

* * * * *